(12) United States Patent
Sarna et al.

(10) Patent No.: US 8,109,960 B2
(45) Date of Patent: Feb. 7, 2012

(54) PATIENT'S SKIN PUNCTURING DEVICE

(75) Inventors: Wojciech Sarna, Warsaw (PL); Andrzej Jankowski, Warsaw (PL); Wojciech Wyszogrodzki, Warsaw (PL)

(73) Assignee: "HTL-Strefa" Spolka Akcy Jna, Ozorkow (PL)

( * ) Notice: Subject to any disclaimer, the term of this patent is extended or adjusted under 35 U.S.C. 154(b) by 102 days.

(21) Appl. No.: 12/518,008

(22) PCT Filed: Jan. 8, 2008

(86) PCT No.: PCT/PL2008/000004
§ 371 (c)(1),
(2), (4) Date: Jun. 5, 2009

(87) PCT Pub. No.: WO2008/085071
PCT Pub. Date: Jul. 17, 2008

(65) Prior Publication Data
US 2010/0318111 A1 Dec. 16, 2010

(30) Foreign Application Priority Data
Jan. 10, 2007 (PL) .......................................... 381512

(51) Int. Cl.
*A61B 5/151* (2006.01)

(52) U.S. Cl. ..................................................... 606/182

(58) Field of Classification Search ................... 606/167, 606/181–185; 600/583
See application file for complete search history.

(56) References Cited

U.S. PATENT DOCUMENTS

| | | | |
|---|---|---|---|
| 4,625,877 A | 12/1986 | Hoch | |
| 5,356,420 A | 10/1994 | Czernecki et al. | |
| 5,439,473 A | 8/1995 | Jorgensen | |
| 5,755,733 A * | 5/1998 | Morita | 606/182 |
| 6,090,124 A * | 7/2000 | Weekes | 606/182 |
| 6,358,265 B1 * | 3/2002 | Thorne et al. | 606/181 |
| 7,297,152 B2 * | 11/2007 | Fukuzawa et al. | 606/181 |
| 7,481,819 B2 * | 1/2009 | Koeppel et al. | 606/182 |
| 2004/0243164 A1 | 12/2004 | D'Agostino | |
| 2004/0260324 A1 * | 12/2004 | Fukuzawa et al. | 606/181 |
| 2006/0241669 A1 * | 10/2006 | Stout et al. | 606/182 |

FOREIGN PATENT DOCUMENTS

JP 05-293069 11/1993
WO WO 2005/009238 A1 2/2005

OTHER PUBLICATIONS

International Search Report Dated Jun. 2, 2008.

* cited by examiner

*Primary Examiner* — Kathleen Sonnett
(74) *Attorney, Agent, or Firm* — Plumsea Law Group

(57) ABSTRACT

A patient's skin puncturing device according to the present invention is built of a body and of seated therein a pricking needle assembly and of a push-button arranged in the upper portion of the body. Between the push-button and the pricking needle assembly at least two driving springs are arranged. The driving springs are connected by upper ends with the push-button provided with a pushing face. Between the body and the pricking needle assembly at least two return springs are disposed, which are connected with the body. The pricking needle assembly has a driving face cooperating with the pushing face of the push-button, and in the upper portion has wings which upper surfaces cooperate with the driving springs of the push-button and which lower surfaces cooperate with the return springs, and has outer projections cooperating with inner projections with which the body is provided.

19 Claims, 6 Drawing Sheets

PATIENT'S SKIN PUNCTURING DEVICE

TECHNICAL FIELD

The subject of the invention is a patient's skin puncturing device, particularly intended to puncture a patient's skin for collecting a blood sample for diagnostic purposes.

BACKGROUND ART

From the U.S. Pat. No. 5,356,420 a puncturing device is known comprising a sleeve and a push button positioned at one sleeve end. The other sleeve end terminates with a bottom with an opening therein. Inside the sleeve a piston is slidably positioned, terminating with a push rod at the end closer to the push button, and with a puncturing tip at the end closer to the bottom opening. Inside the sleeve, between the push button face and the piston a drive spring is located, and between the piston and the sleeve bottom a return spring is placed. The piston comprises wings located on its outer perimeter, which wings rest on an internal projection of the sleeve, and when the device is used, the wings get broken, and subsequent re-use of the device is not possible.

In the U.S. Pat. No. 5,439,473 is disclosed a lancet designed for puncturing the patient's skin for collecting small blood samples. The lancet has an elongated body wherein a movable member is placed slidingly along the body axis, while the body has a top opening for the lancet push button, and a bottom opening for the piercing blade. The movable member consists of a flat spring, one end of which is joined to the push button. The push button has two upper arms perpendicular to its surface, and these arms have hooked ends placed in oblong openings of the body side walls. The other end of the movable member flat spring is joined with a holder wherein the piercing blade is fixed. The lower portion of the holder has two lower arms parallel to the upper arms. The lower arms have, moreover, upwardly directed, triangle shaped ends, which rest upon the lower edges of the oblong openings of the body walls. All parts of the movable member are made of plastic. When the patient's skin is being punctured, the lancet push button is pressed, so the flat spring of the movable member is tensed, and hooked ends of the upper arms press against the ends of the lower arms of the movable member. Next, the lower arms get released, the flat spring rebounds, and the patient's skin is punctured by the piercing blade, which passes through the body bottom opening. After puncturing the skin, the flat spring assumes its free position, and the piercing blade retracts into the inside of the lancet body.

Further, the U.S. Pat. No. 5,755,733 discloses a lancet device consisting of a lancet assembly and a holder linked to the lancet assembly, wherein the lancet assembly has a lancet with a piercing portion, and an ejector which pushes the lancet out. In this known lancet device, the lancet piercing portion is covered with plastic material.

DISCLOSURE OF INVENTION

The purpose of this invention is to provide a disposable patient's skin puncturing device for collecting a blood sample for diagnostic purposes, which is cheap, safe, both for the patient and for service personnel, and easy in use.

Particularly, the purpose of this invention is to provide the patient's skin puncturing device with a structure of a possibly minimal number of elements for decreasing costs of a manufacture of a final product.

The next purpose of this invention is to provide the patient's skin puncturing device devoid of metal springs for further decreasing costs of the manufacture of the final product and for facilitating its utilization after use, which has fundamental importance in the case of devices intended for mass medical applications.

The next purpose of this invention is to provide the patient's skin puncturing device with the structure ensuring an elasticity of inner projections of a body, which is required for correct functioning of the patient's skin puncturing device.

The next purpose of this invention is to provide a patient's skin puncturing device of the structure guaranteeing to get the correct, undamaged inner projections of the body during manufacture of the body, and particularly during sliding a moulding piece down from a male mould in the course of an injection moulding process of the body.

A patient's skin puncturing device according to the present invention is built of a body and of seated therein a pricking needle assembly and of a push-button arranged in the upper portion of the body, wherein between the push-button and the pricking needle assembly at least one driving spring is arranged, and between the body and the pricking needle assembly at least one return spring is arranged. The device has at least two driving springs connected by upper ends with the push-button provided with a pushing face and it has at least two return springs connected with the body, whereas the pricking needle assembly has a driving face cooperating with a pushing face of the push-button, wings situated in the upper portion of the pricking needle assembly, whereas upper surfaces of the wings cooperate with the driving springs of the push-button and lower surfaces of the wings cooperate with the return springs, and the pricking needle assembly further has outer projections cooperating with inner projections with which the body is provided.

Preferably, in the body at the level of the inner projections technological projections are provided, which technological projections have a bigger height than a height of the inner projections for protection of the inner projections from being damaged in the process of forming the moulded piece of the body.

Preferably, the body has an external flange in which apertures are provided for increasing an elasticity of the inner projections of the body.

Preferably, the driving springs are integrally connected with the push-button constituting one element formed in a technological process.

Preferably, the return springs are integrally connected with the body constituting one element formed in a technological process.

The advantage of the patient's skin puncturing device according to the invention is a simplicity of its structure with a small number of structure elements, which enables to get the cheap, easy in use and disposable puncturing device, and thus safe, both for the patient and for service personnel for collecting a blood sample for diagnostic purposes.

The next advantage of the patient's skin puncturing device according to the invention is that it is devoid of metal springs, which decreases the costs of its manufacture and facilitates its utilization after use.

The further advantage of the patient's skin puncturing device according to the invention is that its structure provides the elasticity of the inner projections of the body necessary for correct working of the patient's skin puncturing device.

The next advantage of the patient's skin puncturing device according to the invention is that its structure guarantees getting the correct, undamaged inner projections of the body during manufacture of the body.

Thus, simple structure of the present patient's skin puncturing device with the small number of structural elements and due to plastic springs applied provides the final product, which is cheap and easy in utilization. This aspect of the device according to the present invention has basic significance for disposable puncturing devices intended to be used in mass medical applications.

BRIEF DESCRIPTION OF DRAWINGS

The subject of the invention is presented in an example embodiment on the drawings, where.

BEST MODE OF CARRYING OUT THE INVENTION

Figures 1, 1A, 1B:
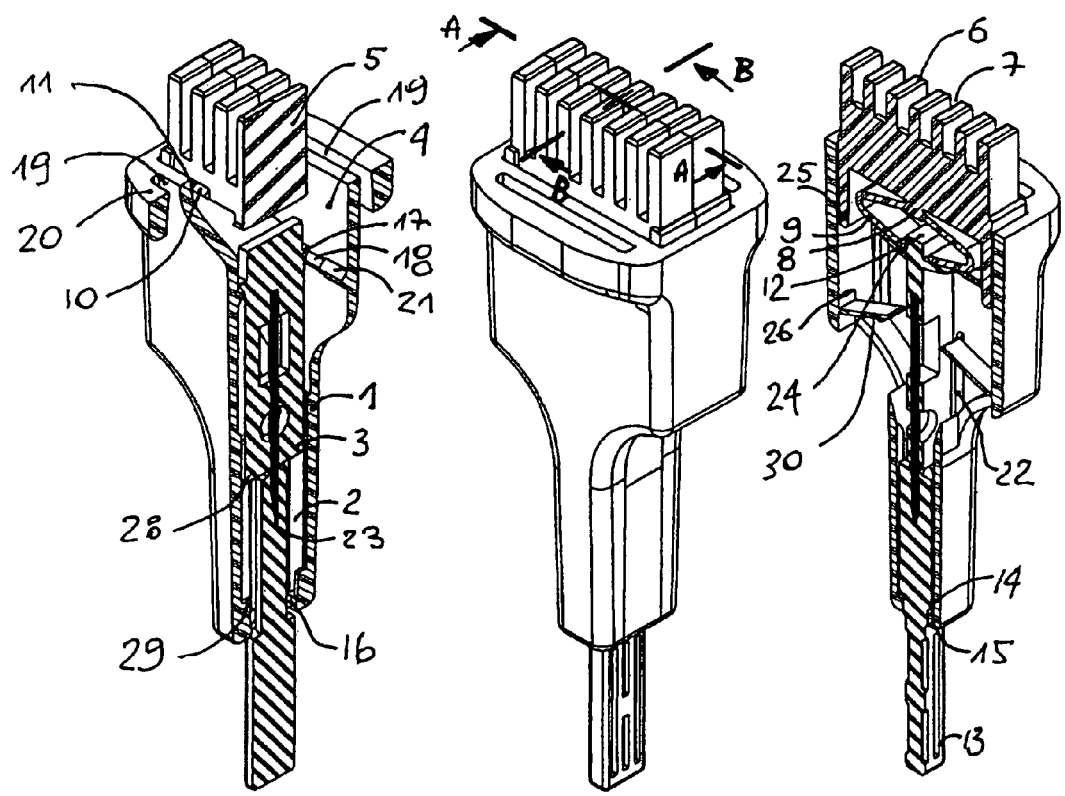
FIG. 1 shows the front, side and top perspective view of the patient's skin puncturing device according to the present invention, before its use.
FIG. 1A shows the section along A-A line of the device of FIG. 1.
FIG. 1B shows the section along B-B line of the device of FIG. 1, FIG. 2—shows the exploded view of the device of FIG. 1 with depicting the device structural elements, FIG. 3A and FIG. 3B—show the device of FIG. 1, in a releasing phase of a pricking needle assembly, respectively, in the section along A-A and B-B lines, FIG. 4A and FIG. 4B—show the device of FIG. 1, in an after release phase of the pricking needle assembly, respectively, in the section along A-A and B-B lines, FIG. 5A and FIG. 5B—show the device of FIG. 1, in a pricking phase of the patient's skin, respectively, in the section along A-A and B-B lines, and FIG. 6A and FIG. 6B—show the device of FIG. 1, in an after pricking phase of the patient's skin, respectively, in the section along A-A and B-B lines.
Figure 2:
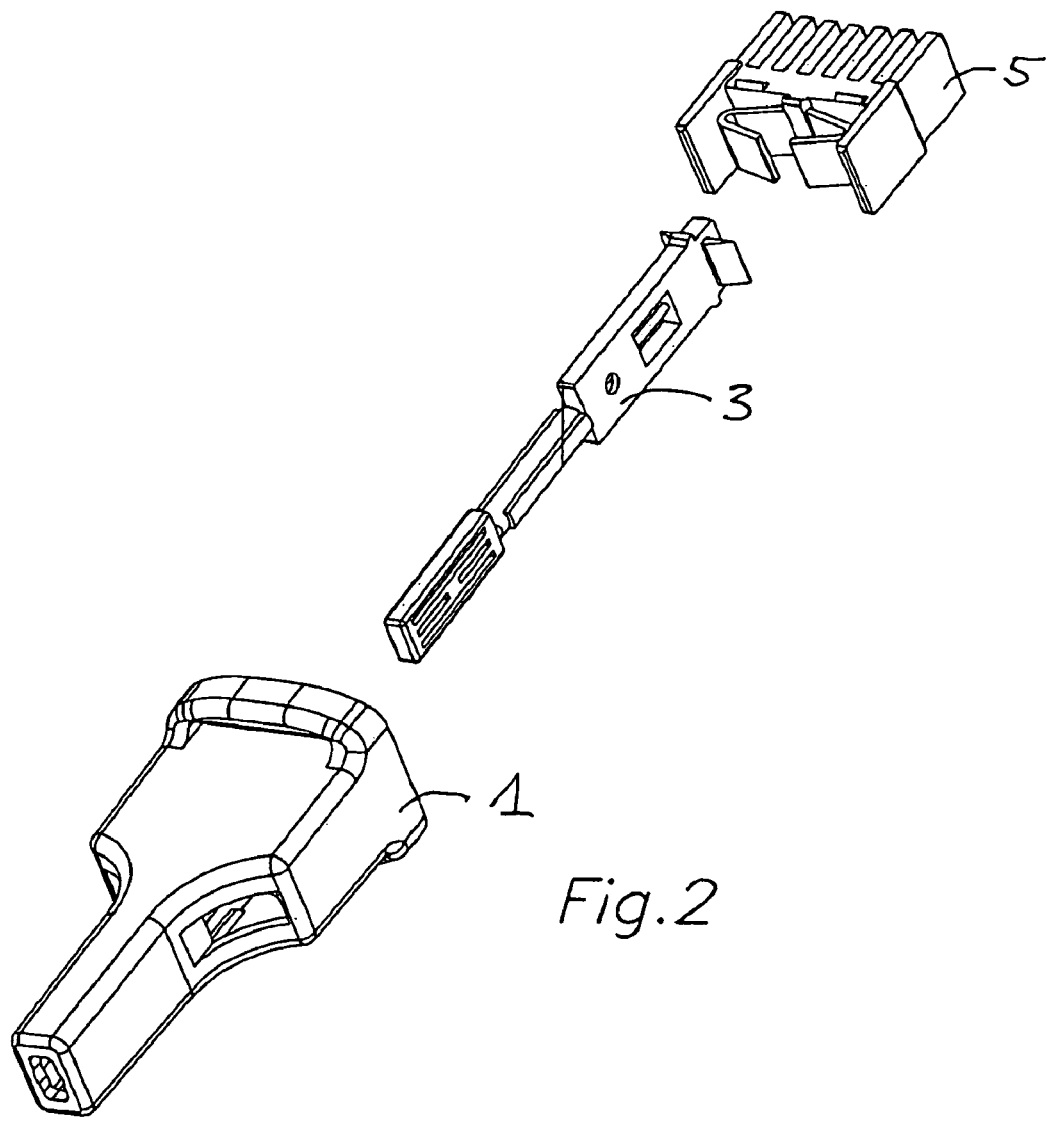

The patient's skin puncturing device according to the invention designed for collecting a sample of blood for diagnostic purposes, as shown in FIGS. 1, 1A and 1B is built of a body 1, in a bottom opening 2 of which a pricking needle assembly 3 is seated and in a top opening 4 of which a push button 5 is seated. The push-button 5 has, in an upper portion, the external thrust face, preferably, shaped in a form of protrusions 6 and pits 7, and, in a lower portion, a pushing face 8 and two driving springs 9. The push-button 5 and the driving springs 9 for minimization of manufacture costs of the device are made as single element in an injection moulding process. The push-button 5 has side catches 10, which rest upon detents 11 of the body 1 and which protect the push-button 5 against falling out of the body 1. The pricking needle assembly 3 has in the upper portion wings 12 which extend laterally. Lower ends of the driving springs 9 abut against upper surfaces of the wings 12 of the pricking needle assembly 3, thereby pressing down a pricking needle sheath 13 with protrusions 14 of the sheath 13 to an abutting edge 15 of an outlet 16 of the body 1. The pricking needle assembly 3 is provided from the front and from the rear with outer projections 17, and the body 1 is on a front internal wall and on a rear internal wall provided with inner projections 18. Due to apertures 19 made in a flange 20 of the body 1, the inner projections 18 preserve respective elasticity in the course of sliding a moulded piece of the body 1 down from a male mould during an injection moulding process of the body 1. Inside the body 1, on its front and rear internal walls, at the level of the inner projections 18 technological projections 21 are provided. The technological projections 21 have bigger height than the inner projections 18. The bigger height of the technological projections 21 protects the inner projections 18 against a damage in the course of sliding the body 1 down from the male mould during the process of forming the moulded piece of the body 1 in an injection mould. In the assembled patient's skin puncturing device according to the present invention, the outer projections 17 of the pricking needle assembly 3 are situated above the inner projections 18 of the body 1. Inside the body 1, in the bottom hole 2 guides 22 are situated, between which the pricking needle assembly 3 is slid in. After twisting and sliding the sheath 13 of the pricking needle out from the outlet 16 of the body 1, a piercing blade 23 of the pricking needle is uncovered. During sliding the sheath 13 of the pricking needle out of the body 1, the pricking needle assembly 3 moves slightly downwards and its outer projections 17 contact with the inner projections 18 of the body 1.

Figures 3A, 3B:
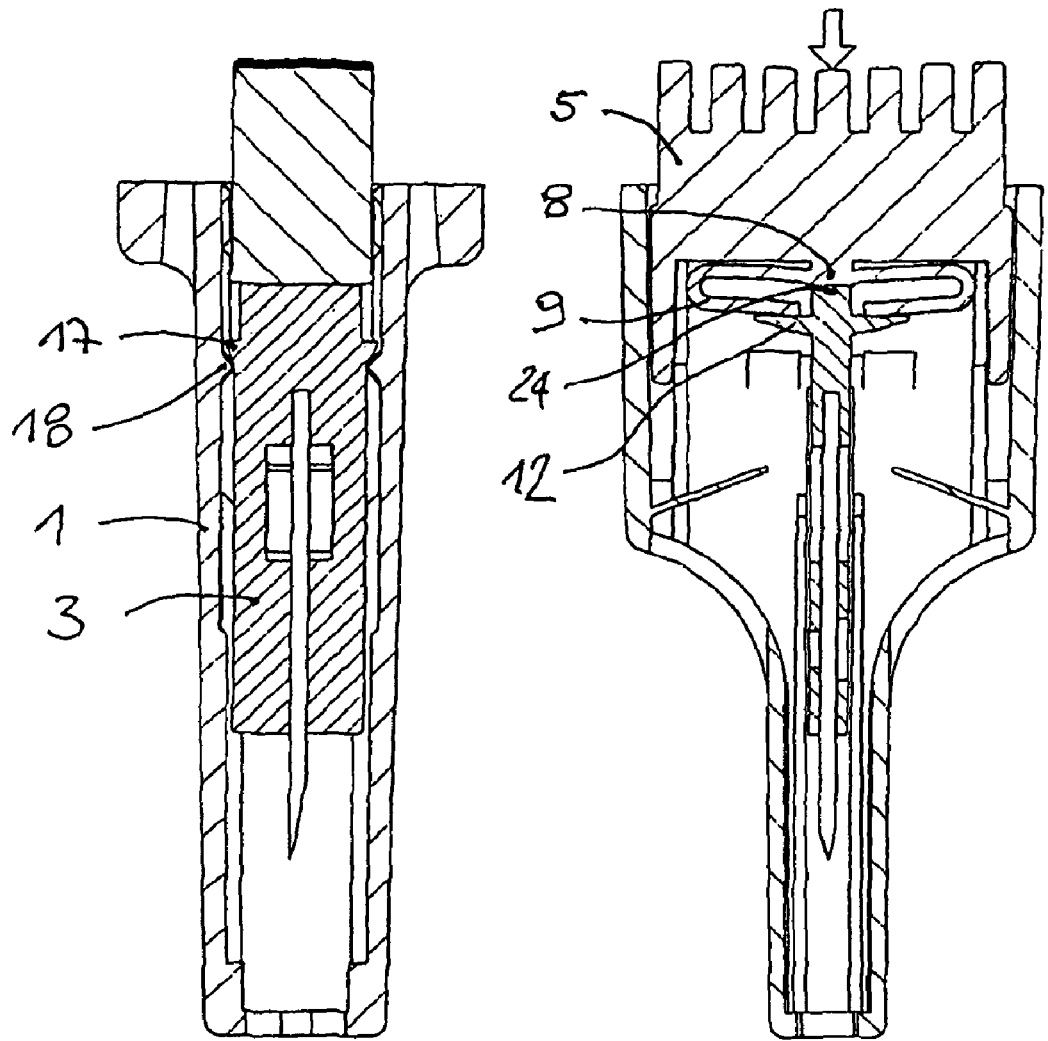

In FIG. 3A and FIG. 3B the patient's skin puncturing device according to the present invention is shown, in the releasing phase of the pricking needle assembly 3. When the push-button 5 is being pushed in, the driving springs 9, which abut against the upper surface of the wings 12 of the pricking needle assembly 3, are deflecting till a moment of a contact of the pushing face 8 of the push-button 5 with a driving face 24 of the pricking needle assembly 3. Farther pushing in the push-button 5 causes displacement of the pricking needle assembly 3 downwards and forcing the outer protrusions 17 of the pricking needle assembly 3 through the inner projections 18 of the body 1 due to their elastic strain induced.

Figures 4A, 4B:
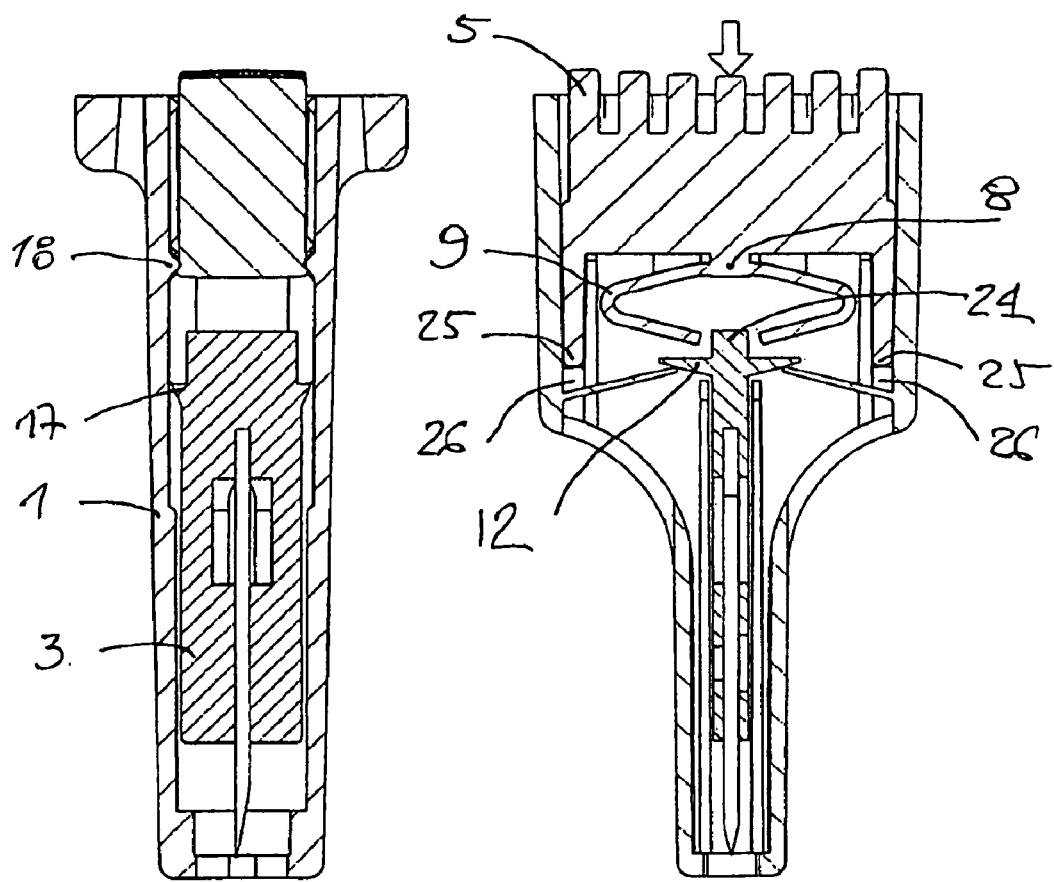

In FIG. 4A and FIG. 4B the patient's skin puncturing device according to the present invention is shown, in an after release phase of the pricking needle assembly 3. When a thrust force is exerted by an user to the external thrust face of the push-button 5, and after forcing the outer protrusions 17 of the pricking needle assembly 3 through the elastic inner projections 18 of the body 1, the push-button 5 contacts by its pushing face 8 with the driving face 24 of the pricking needle assembly 3 and drives the pricking needle assembly 3 till the moment in which the push-button 5 abuts with its lower ends 25 against stops 26 in the body 1. Additionally, the pricking needle assembly 3 is driven by the rebounding driving springs 9 which press the upper surfaces of the wings 12 of the pricking needle assembly 3.

Figures 5A, 5B:
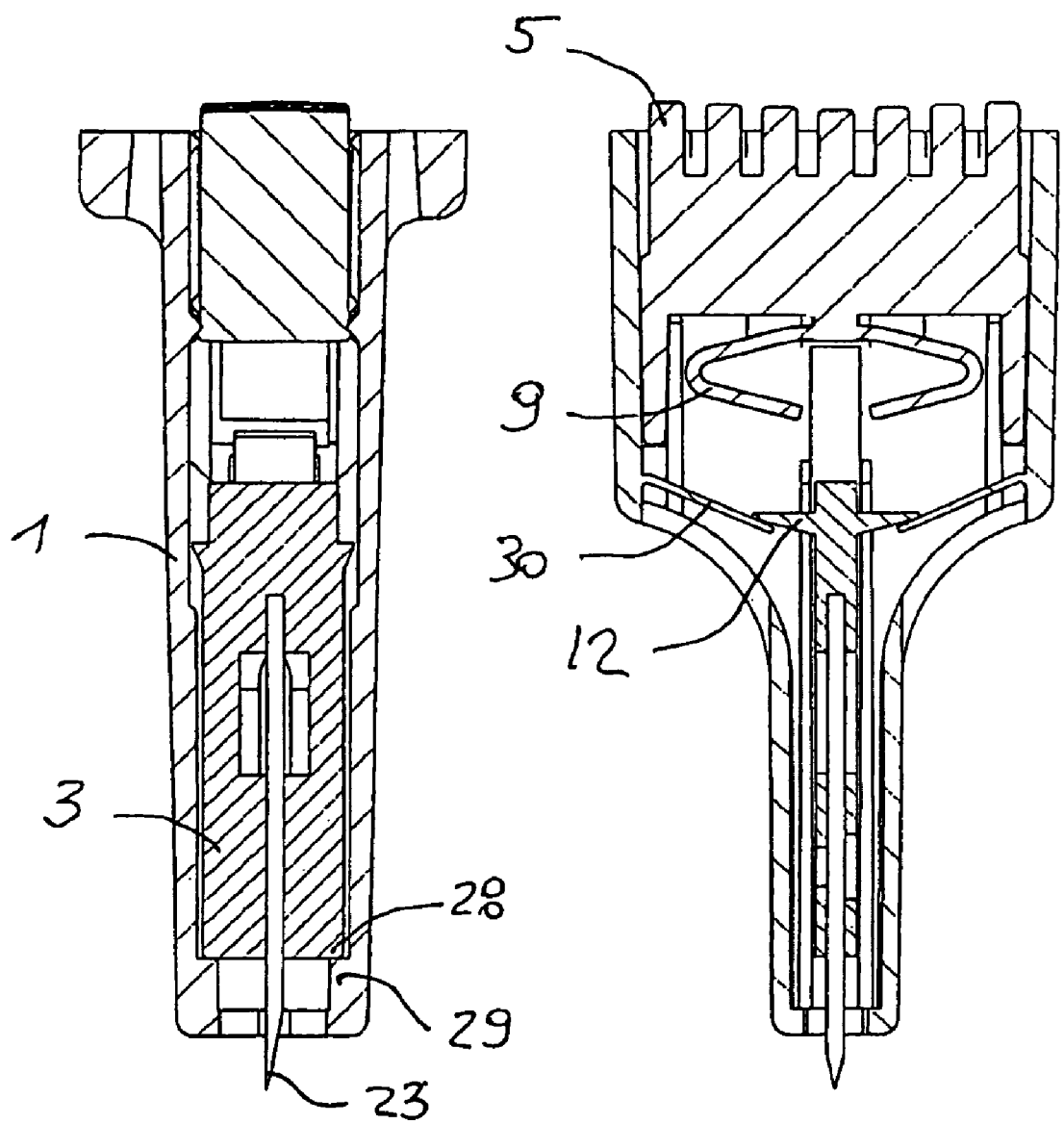

In FIG. 5A and FIG. 5B the patient's skin puncturing device according to the present invention is shown, in a pricking phase of the patient's skin. Under the influence of an energy accepted from the push-button 5 and the rebounded driving springs 9, the pricking needle assembly 3 moves downwards in the body 1 and abuts by its lower stop face 28 against an end stop 29 of the body 1 thereby bending out downwards return springs 30 of the body 1 with lower surfaces of the wings 12. The piercing blade 23 of the pricking needle extends maximal away from the body 1. For minimization of the manufacture costs of the device, the body 1 and the return springs 30 are made as single element in the injection moulding process.

Figures 6A, 6B:
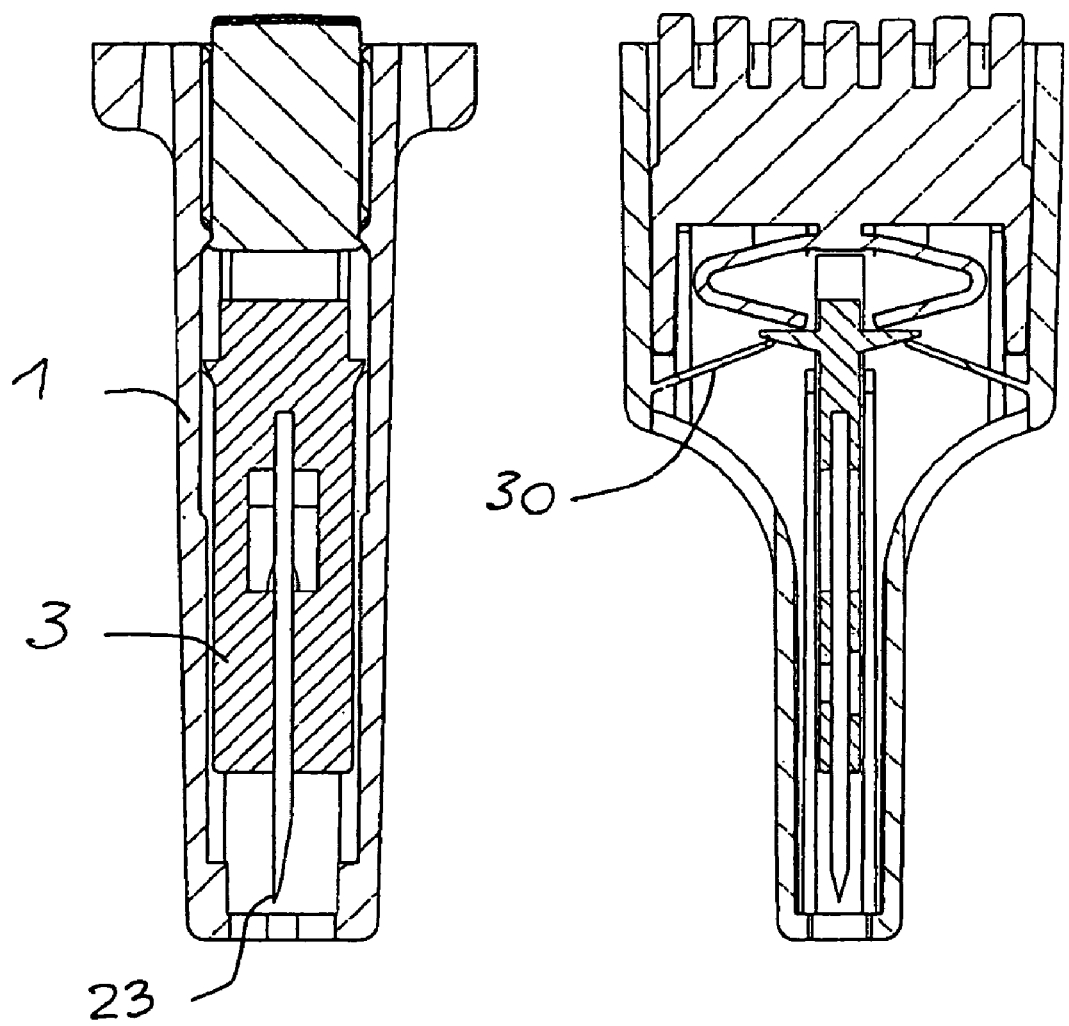

In FIG. 6A and FIG. 6B the patient's skin puncturing device according to the present invention is shown, in an after pricking phase of the patient's skin. Under the energy stored in the return springs 30, which return springs 30 have been bent out downwards in the previous working phase of the device shown in the FIG. 5A and FIG. 5B, the pricking needle assembly 3 moves upwards in the body 1 till the moment of the complete retraction of the piercing blade 23 of the pricking needle in the body 1.

We claim:

1. A patient's skin puncturing device comprising:
a body in which is seated a pricking needle assembly and a push-button arranged in an upper portion of the body, wherein between the push-button and the pricking needle assembly at least two driving springs are arranged, and between the body and the pricking needle assembly at least two return springs are arranged,
wherein the at least two driving springs are connected by upper ends with the push-button provided with a pushing face and the at least two return springs are connected with the body,
wherein the pricking needle assembly has
a driving face cooperating with the pushing face of the push-button,
wings situated in an upper portion of the pricking needle assembly, wherein upper surfaces of the wings cooperate with the driving springs of the push-button and lower surfaces of the wings cooperate with the return springs, and
outer projections cooperating with elastic inner projections with which the body is provided,
wherein in a releasing phase of the pricking needle assembly, the lower surfaces of the wings are separate from the return springs, and
wherein in an after release and pricking phase of the pricking needle assembly, the driving springs contact and push the upper surfaces of the wings in a driving direction toward the return springs and release from contact with the upper surfaces of the wings when the driving springs reach full decompression.

2. The patient's skin puncturing device according to claim 1, wherein in the body adjacent to the inner projections are provided technological projections, wherein the inner projections and the technological projections project from a common base surface, and wherein the technological projections project farther from the common base surface than do the inner projections such that the technological projections protect the inner projections from being damaged during molding of the body.

3. The patient's skin puncturing device according to claim 1, wherein the body and the pricking needle assembly extend in a longitudinal direction, wherein the body has an external flange that extends approximately perpendicularly from a longitudinally extending sidewall of the body, wherein an elastic inner projection of the elastic inner projections is disposed on an interior surface of the sidewall, wherein the external flange defines an aperture between a distal edge of the external flange and the sidewall, and wherein by virtue of the aperture of the external flange, the sidewall deflects in a direction toward the distal edge of the external flange to move the elastic inner projection in a direction away from a longitudinal axis of the pricking needle assembly to allow an outer projection of the outer projections of the pricking needle assembly to pass by.

4. The patient's skin puncturing device according to claim 3, wherein when viewed in a direction along the longitudinal direction the external flange is rectangular with two longer sides and two shorter sides, and wherein the sidewall is on one of the two longer sides.

5. The patient's skin puncturing device according to claim 3, wherein the external flange is disposed on a grip end of the body opposite to a puncturing end of the body from which a needle of the pricking needle assembly emerges.

6. The patient's skin puncturing device according to claim 1, wherein the driving springs and the push-button are integrally formed as a single continuous part.

7. The patient's skin puncturing device according to claim 1, wherein the return springs and the body are integrally formed as a single continuous part.

8. The patient's skin puncturing device according to claim 1, wherein the at least two driving springs are directly connected by the upper ends with the push-button provided with the pushing face and the at least two return springs are directly connected with the body.

9. The patient's skin puncturing device according to claim 1, wherein in the after release and pricking phase of the pricking needle assembly, the lower surfaces of the wings contact the return springs and bend the return springs in the driving direction,
wherein in an after pricking phase, the return springs rebound and push the lower surfaces of the wings in a retraction direction opposite to the driving direction to move the pricking needle assembly in the retraction direction.

10. The patient's skin puncturing device according to claim 9, wherein in the after pricking phase, the pricking needle assembly comes to rest with the upper surfaces of the wings contacting the driving springs and the lower surfaces of the wings contacting the return springs, with the driving springs pushing the upper surfaces of the wings in the driving direction and the return springs pushing the lower surfaces of the wings in the retraction direction.

11. The patient's skin puncturing device according to claim 1, wherein a first outer projection of the outer projections is disposed on a first surface of the pricking needle assembly, wherein a second outer projection of the outer projections is disposed on a second surface of the pricking needle assembly, wherein a first wing of the wings is disposed on a third surface of the pricking needle assembly, wherein a second wing of the wings is disposed on a fourth surface of the pricking needle assembly, and wherein the first and second surfaces are perpendicular to the third and fourth surfaces.

12. The patient's skin puncturing device according to claim 1, wherein each wing comprises a single elongated member that extends transversely to a longitudinal axis of the pricking needle assembly, and wherein an upper surface of the single elongated member contacts a driving spring of the at least two driving springs and a lower surface of the single elongated member contacts a return spring of the at least two return springs.

13. The patient's skin puncturing device according to claim 1, wherein the at least two return springs comprise two return springs,
wherein each return spring of the two return springs comprises an elongated member that, in an original unloaded position, extends from the body in an upward direction away from the driving direction and toward a longitudinal axis of the pricking needle assembly, and
wherein the two return springs are symmetrical with respect to the longitudinal axis of the pricking needle assembly.

14. The patient's skin puncturing device according to claim 13, wherein the at least two driving springs comprise two driving springs,
wherein each driving spring of the two driving springs comprises an elongated member that extends from the push-button first in a downward direction toward the driving direction and away from the longitudinal axis of the pricking needle assembly and then folds back toward the longitudinal axis and continues in the downward direction, and wherein the two driving springs are symmetrical with respect to the longitudinal axis of the pricking needle assembly.

15. A patient's skin puncturing device comprising:
a body having an upper portion and a lower portion, wherein the body comprises:
  an elastic inner projection on an interior surface of a wall of the body, and
  a return spring integrally formed on an inside surface of the lower portion of the body;
a pricking needle assembly disposed inside the body and extending in a longitudinal direction, wherein the pricking needle assembly comprises:
  a driving face,
  a wing, and
  an outer projection;
a push-button arranged in the upper portion of the body, wherein the push-button comprises:
  a pushing face configured to push the driving face of the pricking needle assembly, and
  an integrally formed driving spring configured to contact the wing of the pricking needle assembly;
wherein in a releasing phase with an increasing force applied to the push-button, the pushing face pushes against the driving face, the driving spring is compressed between the push-button and the wing, the outer projection contacts the elastic inner projection, and the wing is separated from the return spring,
wherein when the increasing force increases enough to deflect the elastic inner projection, the outer projection passes by the elastic inner projection, and the driving spring decompresses and pushes the wing, to drive the pricking needle assembly in a driving direction moving the wing toward the return spring,
wherein in an after release and pricking phase, the driving spring separates from the wing when the driving spring reaches full decompression, and the wing contacts the return spring and bends the return spring in the driving direction, and
wherein in an after pricking phase, the return spring rebounds and pushes the wing in a retraction direction opposite to the driving direction to move the pricking needle assembly in the retraction direction.

16. The patient's skin puncturing device according to claim 15, wherein the wall of the body is deformable to allow the elastic inner portion to deflect to allow the outer projection to pass by.

17. The patient's skin puncturing device according to claim 15, wherein the body further comprises an external flange member that projects from the wall and encloses an aperture between the external flange member and the wall, such that the wall is capable of deflecting toward the external flange member.

18. The patient's skin puncturing device according to claim 15, wherein in the after pricking phase, the pricking needle assembly comes to rest with the wing contacting both the driving spring and the return spring, with the driving spring pushing the wing in the driving direction and the return spring pushing the wing in the retraction direction.

19. The patient's skin puncturing device according to claim 15, wherein the wing comprises a single elongated member that extends transversely to a longitudinal axis of the pricking needle assembly, and wherein an upper surface of the single elongated member contacts the driving spring and a lower surface of the single elongated member contacts the return spring.

* * * * *